United States Patent

Hattori et al.

[11] Patent Number: 5,820,557
[45] Date of Patent: Oct. 13, 1998

[54] BLOOD GLUCOSE MEASUREMENT APPARATUS

[75] Inventors: Tomohiko Hattori, Nagoya; Norihiko Ushizawa, Fujinomiya, both of Japan

[73] Assignee: Terumo Kabushiki Kaisha, Tokyo, Japan

[21] Appl. No.: 810,334

[22] Filed: Feb. 27, 1997

[30] Foreign Application Priority Data

Mar. 1, 1996 [JP] Japan .................................. 8-044684

[51] Int. Cl.$^6$ ........................................................ A61B 5/00
[52] U.S. Cl. ........................................................ 600/319
[58] Field of Search .................................. 600/316, 318, 600/319, 322, 473, 476

[56] References Cited

U.S. PATENT DOCUMENTS

| | | |
|---|---|---|
| 3,958,560 | 5/1976 | March . |
| 4,877,322 | 10/1989 | Hill ........................................ 600/318 |
| 4,883,351 | 11/1989 | Weiss . |
| 4,895,159 | 1/1990 | Weiss . |
| 5,025,785 | 6/1991 | Weiss . |
| 5,028,787 | 7/1991 | Rosenthal et al. ........................ 250/343 |
| 5,070,874 | 12/1991 | Barnes et al. ............................ 600/322 |
| 5,318,022 | 6/1994 | Taboada et al. . |
| 5,361,758 | 11/1994 | Hall et al. ............................... 600/322 |
| 5,372,136 | 12/1994 | Steuer et al. ............................ 600/476 |

FOREIGN PATENT DOCUMENTS

| | | |
|---|---|---|
| 0 589 191 A1 | 3/1994 | European Pat. Off. . |
| WO 93/07801 | 4/1993 | WIPO . |

*Primary Examiner*—Jennifer Bahr
*Assistant Examiner*—Eric F. Winakur
*Attorney, Agent, or Firm*—Burns, Doane, Swecker & Mathis, LLP

[57] ABSTRACT

A handy blood glucose measurement apparatus irradiates the retina of the eye of the subject with light emitted from light-emitting elements having two different wavelengths, with the light of one wavelength serving as reference light and the light of the other wavelength serving as measurement light. The intensity of the reference light and of the measurement light is obtained and the blood glucose value of the subject is found based upon the difference between these two reflected-light intensities. By focusing his or her eye on a symbol or figure displayed on a display panel in the apparatus, the subject is capable of focusing the light emitted by the light-emitting elements on the retina of the eye in reliable fashion.

7 Claims, 7 Drawing Sheets

BLOOD GLUCOSE MEASUREMENT APPARATUS

BACKGROUND OF THE INVENTION

This invention relates to a blood glucose measurement apparatus that is non-invasive and does not rely upon a blood sample method.

A well-known example of a blood glucose measurement apparatus which uses a non-blood sample method is percutaneous measurement that entails irradiating the surface of the skin of a fingertip or earlobe with infrared laser beam and measuring the beam that is reflected or transmitted. However, owing to the opaqueness of skin, differences in pigmentation from one individual to another and differences in amount of fat, the light sensed tends to contain considerable noise and disparities appear in the results of measurement, thereby rendering such measurement inaccurate.

In an effort to solve this problem, International Publication Number WO 93/07801 discloses an apparatus for measuring glucose concentration in blood by irradiating the surface of the eye with infrared light and sensing the spectrum of the reflected irradiating light. However, what is measured directly by WO 93/07801 is glucose concentration in the eyeball. Consequently, it is likely that the sensed value will differ from the glucose concentration, i.e. the blood glucose value, in blood. This will be described with reference to FIG. 6.

FIG. 6 illustrates the results of monitoring a change in glucose concentration in blood plasma and in an aspirated exudate when an OGTT (Oral Glucose Tolerance Test) under a glucose load of 75 g was conducted using an ISFET-type glucose sensor. It will be appreciated that the change in glucose concentration in the aspirated exudate deviates somewhat from the change in glucose concentration in blood plasma and lags behind by about 10 minutes. The change in glucose concentration in the eyeball thus involves an error in comparison with the blood glucose value in blood and the results of measuring glucose concentration in the eyeball involve a time lag. Accordingly, such an apparatus has serious disadvantages for a diabetic individual who is required to measure blood glucose at every meal and adjust the amount of insulin to be administered.

SUMMARY OF THE INVENTION

The present invention has been devised in view of the examples of the prior art described above and its object is to provide a blood glucose measurement apparatus capable of measuring blood glucose value accurately by applying measurement to blood vessels in the retina of the eye.

Another object of the present invention is to provide a blood glucose measurement apparatus which irradiates blood vessels in the retina of the eye with light from outside the cornea and measures blood glucose based upon the intensity of the reflected irradiating light.

Still another object of the present invention is to provide a blood glucose measurement apparatus capable of measuring blood glucose accurately by using light of a wavelength that is sensitive to glucose concentration in blood and reference light of a wavelength that is unaffected by glucose concentration, and eliminating the effects of passage of light through the eyeball by relying upon a difference between the reflected light intensities of the two irradiating light rays.

A further object of the present invention is to provide a blood glucose measurement apparatus so adapted that the subject can verify, by himself or herself, whether the irradiating light is in focus accurately on the retina at the time of measurement.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principle of the invention.

DESCRIPTION OF THE PREFERRED EMBODIMENTS

Figure 1:
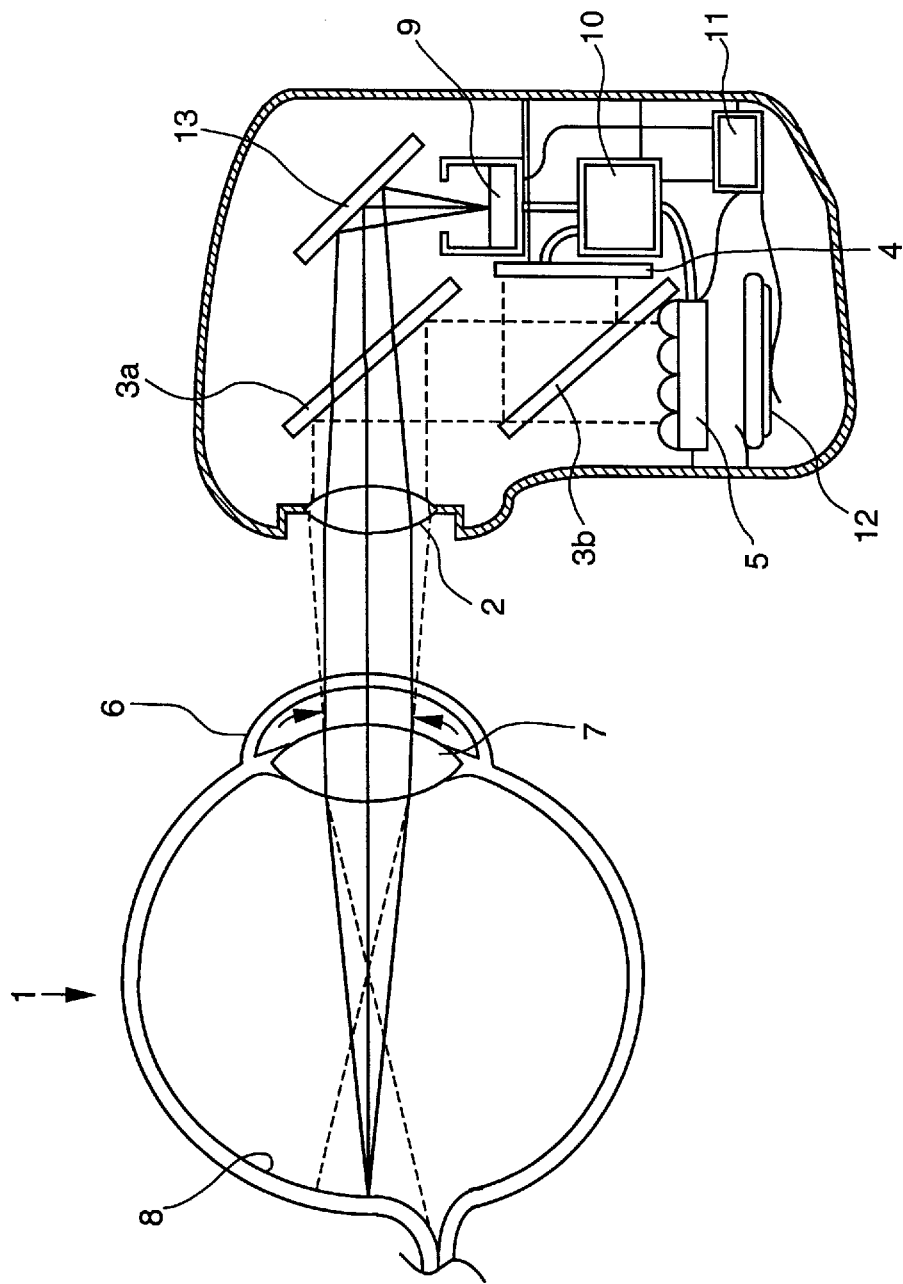
FIG. 1 is a schematic view in which a blood glucose measurement apparatus according to an embodiment of the invention is seen from the side when in use.

Preferred embodiments of the present invention will now be described in detail with reference to the accompanying drawings. Identical elements in the drawings are designated by like reference characters.

FIG. 1 is a schematic view showing the construction of a blood glucose measurement apparatus according to an embodiment of the present invention.

The blood glucose measurement apparatus includes a convex lens 2, half-mirrors 3a, 3b acting as beam splitters, a light-emitting display panel 4, a light-emitting element 5 serving as irradiating means which emits reference light and near-infrared measurement light, a light sensor 9, a processing circuit 10, a regulator or converter 11, a battery 12 and a mirror 13. By observing (focusing on) an image, which is displayed on the light-emitting display panel 4 via the convex lens 2 and half-mirrors 3a, 3b, with his or her own eye 1, the subject is capable of verifying that the reference light and near-infrared light emitted by the light-emitting element 5 is focused on the retina 8 of the eye via the half-mirrors 3a, 3b, convex lens 2, cornea 6 and lens 7.

As shown in FIG. 1, the light-emitting display panel 4, light-emitting element 5 and light sensor 9, which senses the reflected-light intensity of the reference light and measurement light, are placed on the optic axis of the convex lens 2. The reference light and measurement light which has reached the retina 8 is reflectively scattered by the retina 8 so as to reach the light sensor 9 via the lens 7, cornea 6, convex lens 2, half-mirror 3a and mirror 13. The light-emitting display panel 4 displays the image of a photograph or character illuminated as by back-lighting. It will suffice if the panel is a light-emitting plate bearing a slide photograph, character or symbol. Alternatively, as will be described later, the panel may also serve as an indicator for indicating a blood glucose value that has been measured. When the subject can see this image clearly, this means that the reference light and near-infrared measurement light rays are in focus on the retina.

It is preferred that visible light of wavelength 650~670 nm, which is light not readily susceptible to the effects of a change in blood glucose value, be used as the reference light, and that near-infrared light of wavelength 800~1300 nm, namely light whose reflected-light intensity varies sensitively with a change in blood glucose value, be used as the measurement light. The light sensor 9, which is means for identifying these two types of light, can be a sensor array provided with wavelength filters (not shown) that pass only the wavelengths of the reference light and measurement light. Another possible arrangement is to emit these two types of light in the form of pulses having different intervals and distinguish between the two types of light based upon the pulse intervals.

Figure 2:
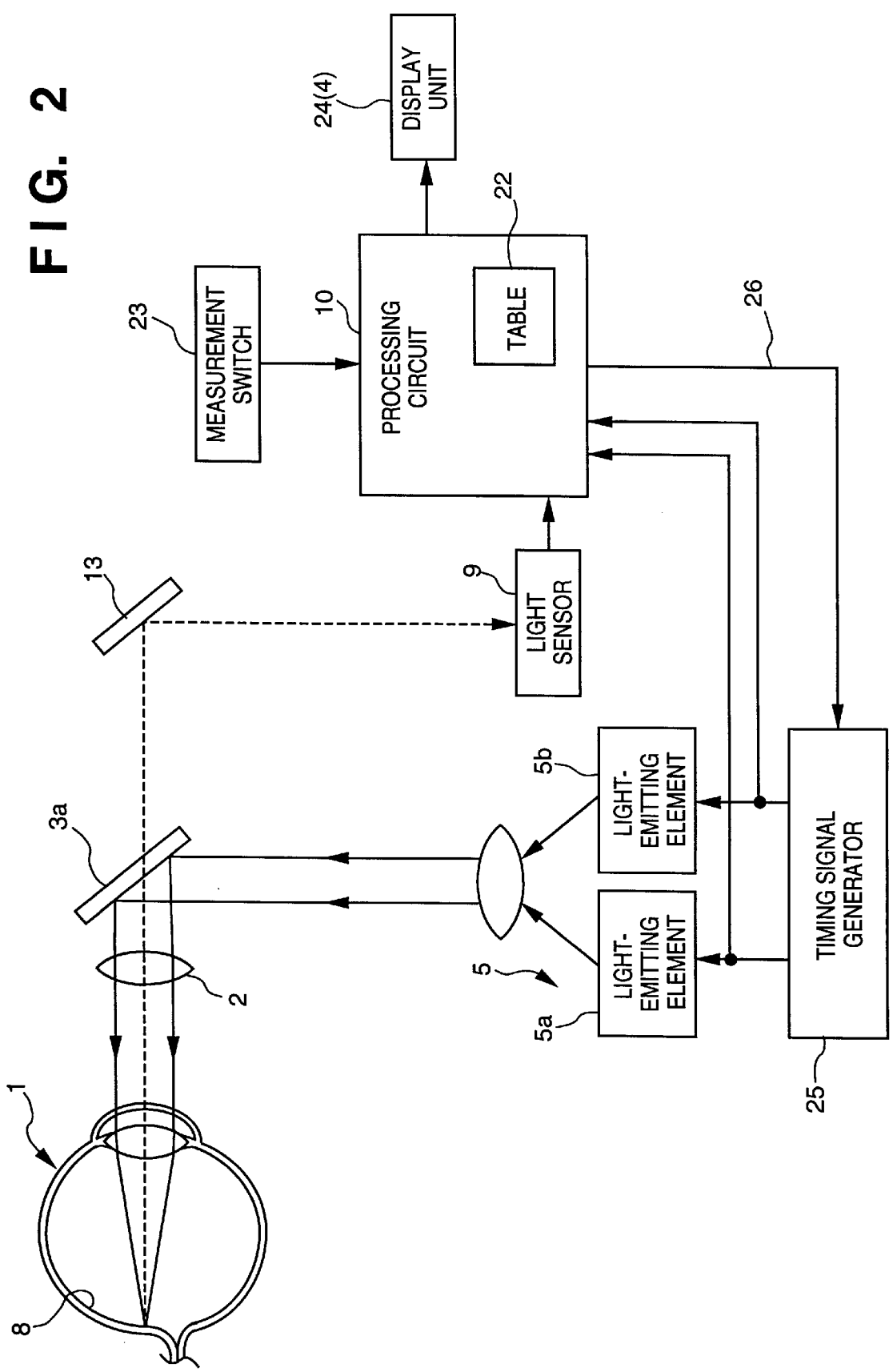
FIG. 2 is a block diagram illustrating the construction of the blood glucose measurement apparatus according to this embodiment.

The processing circuit 10 obtains the blood glucose value based upon the difference between the intensity of the reflected reference light and the intensity of the reflected measurement light, where the intensity is sensed by the light sensor 9. The measured blood glucose value is displayed on the light-emitting display panel 4. Furthermore, these elements and circuitry are supplied with power from the battery 12 via the regulator or converter 11. The half-mirrors 3a, 3b may be beam splitters comprising dichroic mirrors or prisms to raise the efficiency with which light is utilized. Further, the measured blood glucose value may be displayed on another display device (24; FIG. 2) or it may be transmitted to another piece of equipment by cable or radio.

It should be noted that the wavelengths and composition of the reference light and measurement light as well as the shape, size and construction of the apparatus maybe modified without departing from the scope and spirit of the invention.

FIG. 2 is a block diagram showing an example of the construction of a blood glucose measurement apparatus according to this embodiment. In the arrangement illustrated, two light-emitting elements 5a, 5b which emit light of mutually different wavelengths are used, and measurement is performed by causing these two elements to emit light at mutually different timings.

In FIG. 2, the light-emitting element 5a emits reference light of wavelength 650~670 nm and the light-emitting element 5b emits measurement light of wavelength 1000 nm, by way of example. A timing signal generator 25 drives the light-emitting elements 5a, 5b alternately at timings that differ from each other. The driving signals enter the processing circuit 10. A reflected-light intensity signal, which has been sensed by the light sensor 9 in accordance with the timings of the driving signals, also enter the processing circuit 10. As a result, the processing circuit 10 is capable of obtaining the reflected-light intensity of each of the measurement and reference light rays. A measurement switch 23 is used to specify the start of measurement. A display unit 24 is for displaying the results of measurement. The aforementioned display panel 4 may be provided with this function if desired. A table 22 stores data for determining the blood glucose value of the subject based upon the difference between the reflected reference light intensity and the reflected measurement light intensity.

When the blood glucose measurement apparatus is used, the subject (user) presses the switch 23, whereupon the processing circuit 10 starts the measurement operation, issues a signal 26 in response to which the timing signal generator 25 begins driving the light-emitting elements 5a, 5b, and causes the display panel 4 to emit light and display an image or a symbol. When the subject verifies that the measurement light is focused on the retina of the eye and then opens (turns off) the switch 23 in order to designate measurement, the reflected-light intensities of the measurement light and reference light sensed by the light sensor 9 are obtained and the difference between these is then found. The blood glucose value of the subject can be obtained by referring to the table 22 based upon the difference.

Figure 4:
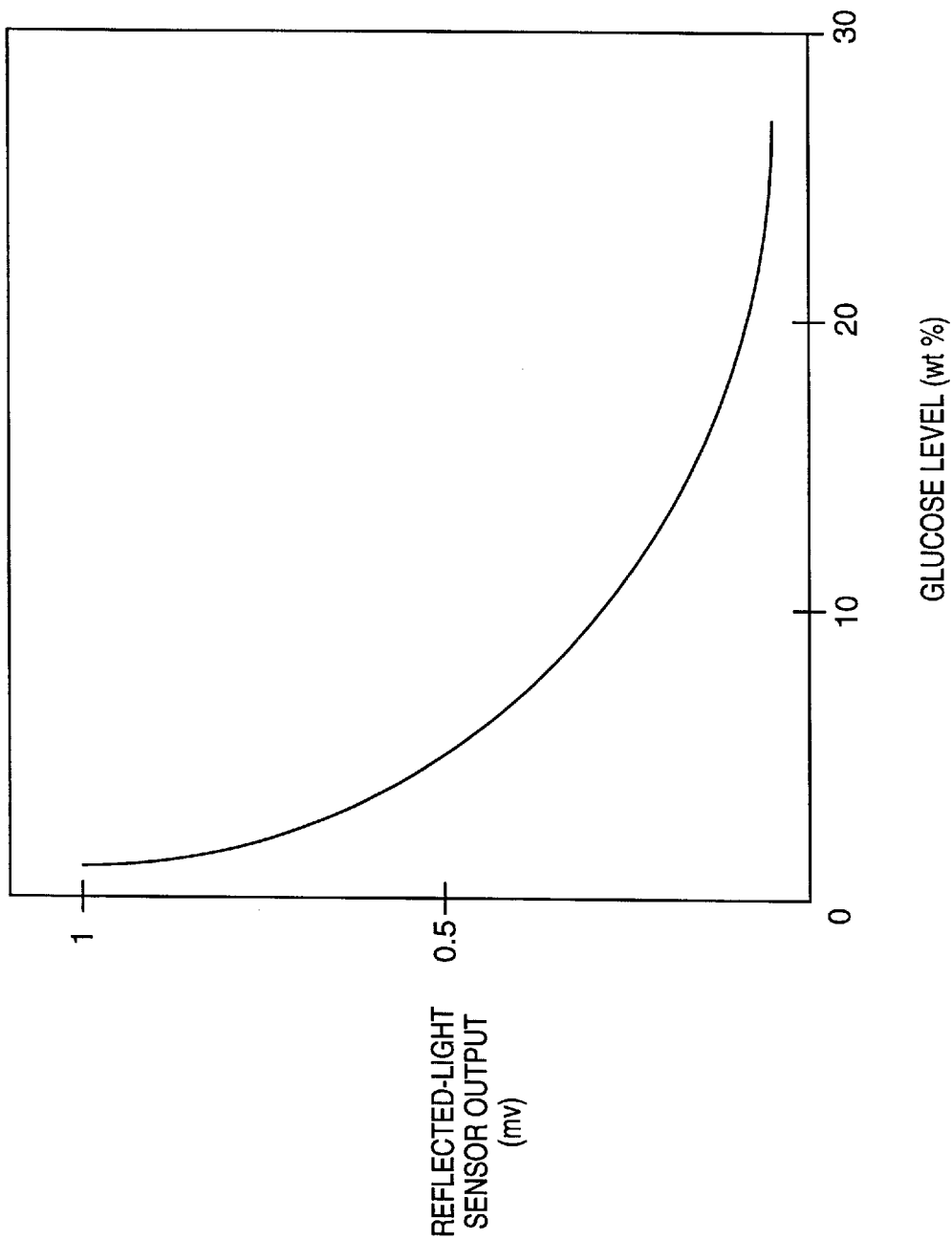
FIG. 4 is a graph showing the relationship between glucose concentration and intensity of reflected light.

FIG. 4 is a graph useful in describing the data in table 22.

FIG. 4 is a graph illustrating the relationship between glucose concentration in an aqueous solution and intensity of reflected light when this aqueous solution is irradiated with light of wavelength 1000 nm, by way of example.

The graph clearly shows that an increase in glucose concentration is accompanied by a decrease also in the intensity of reflected light, because the amount of light absorption is increased by glucose. If we let x represent the intensity of reflected measurement light and y the intensity of reflected reference light, then the difference α of the former to the latter will be as expressed by the following equation:

$$\alpha = (y+d)-(x+c) \qquad \ldots (1)$$

where c and d are correction constants.

The relationship between the reflected-light intensity difference α and the glucose concentration value may be considered to have a characteristic based on that of the graphed characteristic if FIG. 4. Accordingly, the relationship between the reflected-light intensity difference α and the actual glucose concentration value (blood glucose value) is obtained and the results are stored in the table 22 in advance. Then, by referring to the table 22 based upon the reflected-light intensity difference obtained for each measurement, the blood glucose value of the subject can be determined.

Figure 3:
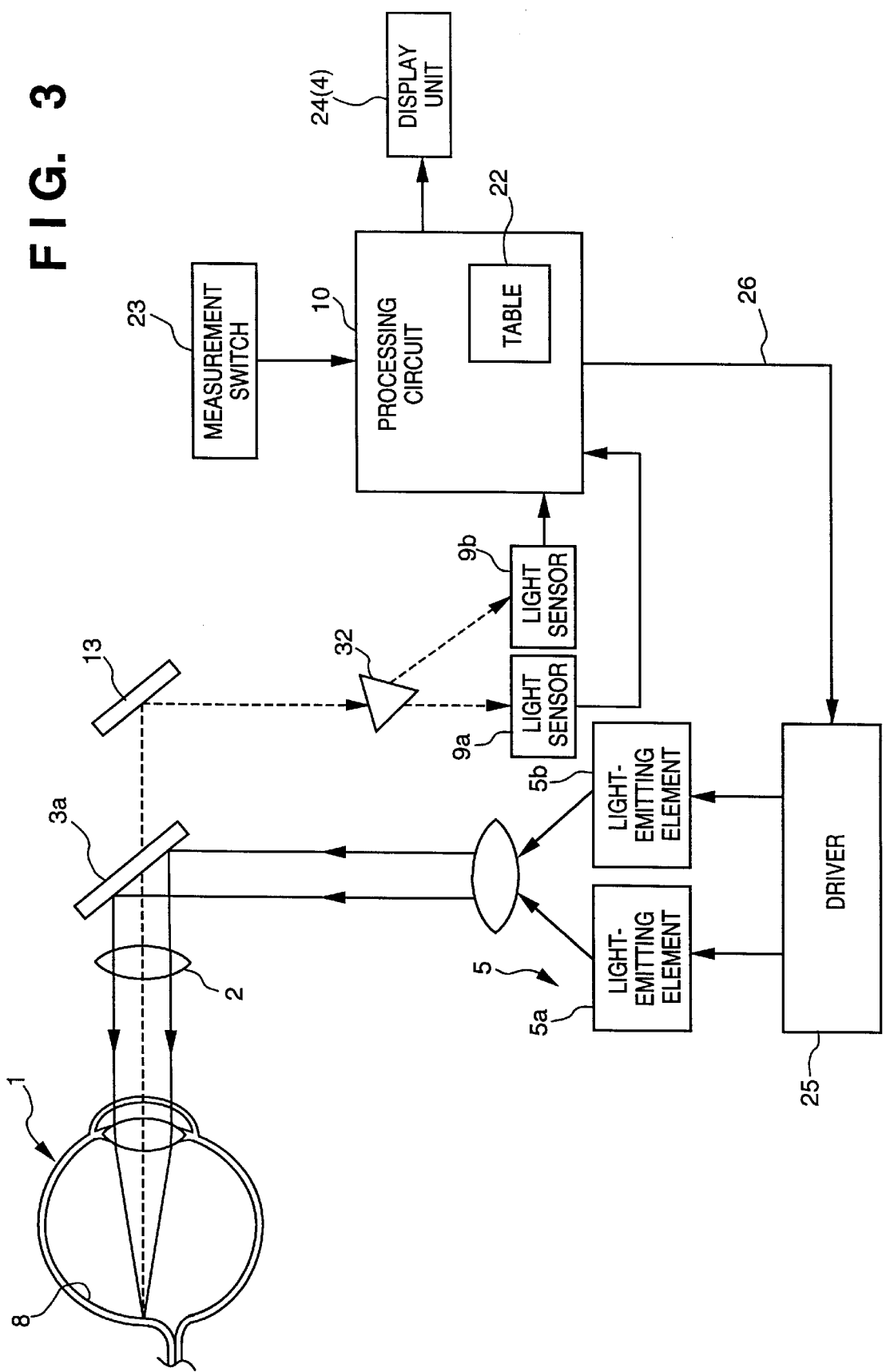
FIG. 3 is a block diagram showing another example of the construction of the blood glucose measurement apparatus according to this embodiment.

FIG. 3 is a block diagram illustrating another example of the construction of the blood glucose measurement apparatus according to this embodiment.

In this example the light-emitting elements 5a, 5b are driven simultaneously by a driver 31, a spectroscope 32 is provided for classifying and extracting light of at least two wavelengths, and it is so arranged that the reflected light of the wavelength emitted by the light-emitting element 5a enters a light sensor 9a and the reflected light of the wavelength emitted by the light-emitting element 5b enters a light sensor 9b. As a result, rather than the light-emitting elements 5a, 5b being driven in time-shared fashion as in the above-described arrangement, here they are driven simultaneously to obtain the intensities of the reflected light. Other processing is similar to that described above in connection with FIG. 2 and need not be described again.

Figure 5:
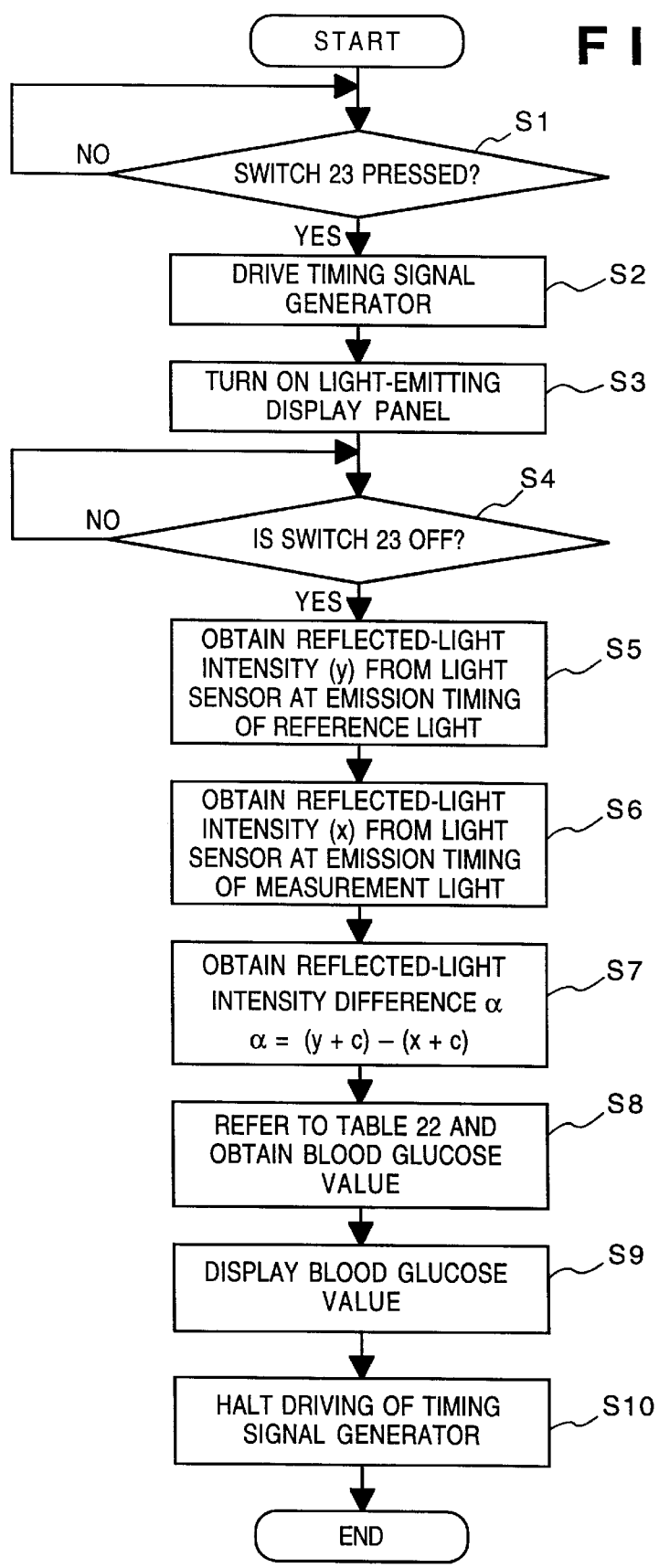
FIG. 5 is a flowchart illustrating measurement processing executed by the blood glucose measurement apparatus of this embodiment.
Figure 6:
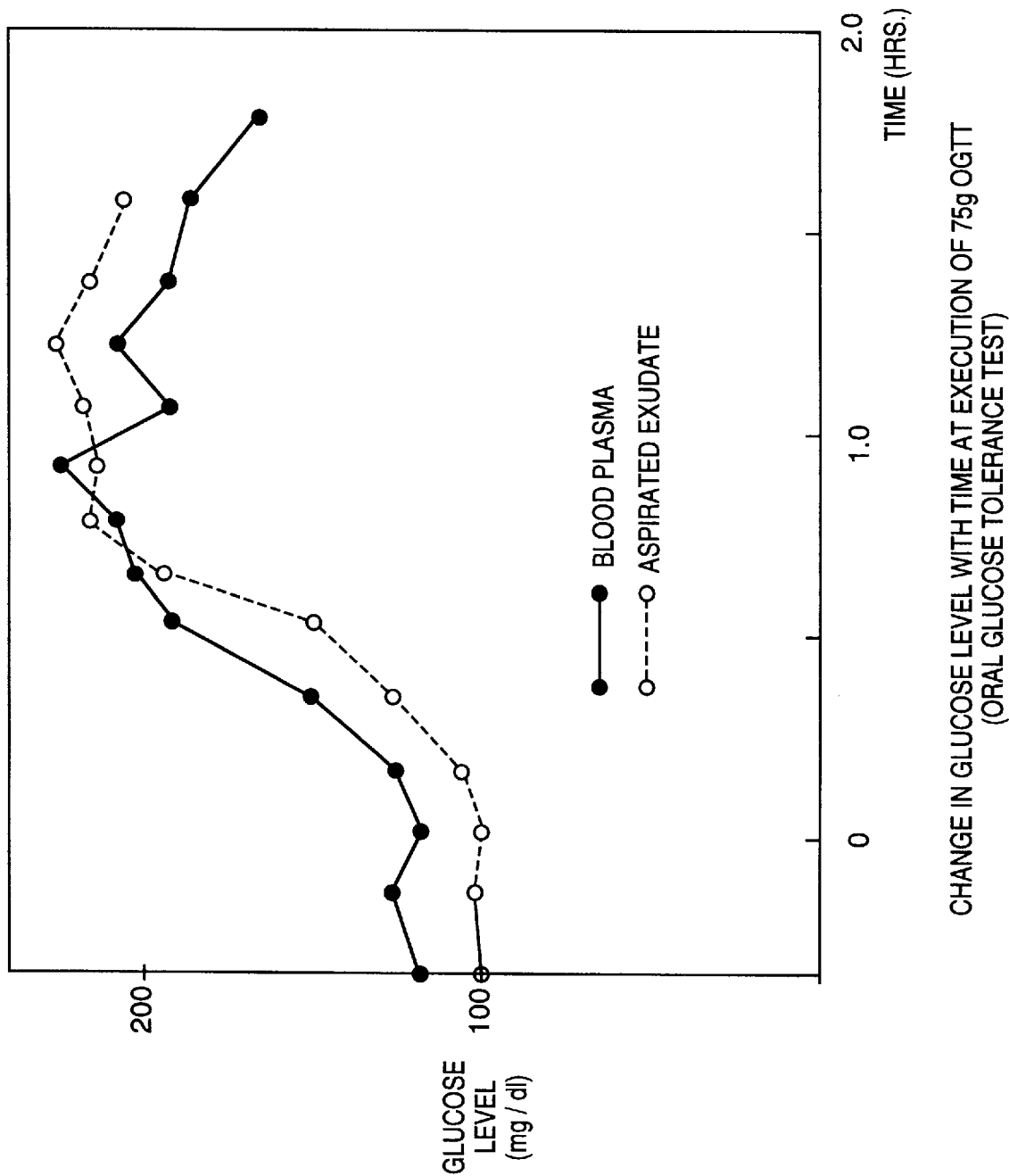
FIG. 6 is a diagram showing a change in glucose concentration in blood and in an aspirated exudate.

FIG. 5 is a flowchart of measurement processing executed by the processing circuit 10 in the blood glucose measurement apparatus of this embodiment.

When the measurement designating switch 23 is pressed at step S1, the program proceeds to step S2, where the timing signal generator 25 is driven into operation so as to cause the light-emitting elements 5a, 5b to emit light. The light-emitting display panel 4 is then lit at step S3. While depressing the switch 23, the subject (user) confirms that the light is focused on the retina and then releases the switch 23 (step S4). As a result, the program proceeds from step S4 to step S5, at which measurement is started.

Specifically, based upon a reference-light emission timing signal entering from the timing signal generator 25, the reflected-light intensity (y) sensed by the light sensor 9 in accordance with this timing enters the processing circuit 10 at step S5. Similarly, at step S6, based upon a measurement-light emission timing signal entering from the timing signal generator 25, the reflected-light intensity (x) sensed by the light sensor 9 in accordance with this timing enters the processing circuit 10. This is followed by step S7, at which the reflected-light intensity difference (α) is obtained from these two reflected-light intensities in accordance with Equation (1). Next, at step S8, the table 22 is looked up based upon the reflected-light intensity difference obtained, whereby the measured blood glucose value is determined. This blood glucose value is displayed on the display unit 24 (4) at step S9. Then, at step S10, drive of the light-emitting elements 5a, 5b is halted and so is the light emission from the display panel 4. (However, when the measured blood glucose value is being displayed on the display panel 4, the panel 4 remains lit.) Further, the blood glucose value displayed on the display unit 24 (4) vanishes automatically when the apparatus is not operated for a prescribed period of time.

With the blood glucose measurement apparatus having the arrangement shown in FIG. 3, the intensity of reflected light sensed by the light sensor 9a is read at step S5 and the intensity of reflected light sensed by the light sensor 9b is read at step S6. This makes it possible to obtain the intensity of the reflected reference light and the intensity of the reflected measurement light. Other processing is the same as that described.

With this arrangement, almost no power is consumed except at such time that measurement is taken. This makes it possible to prolong the service life of the battery 12.

Figure 7:
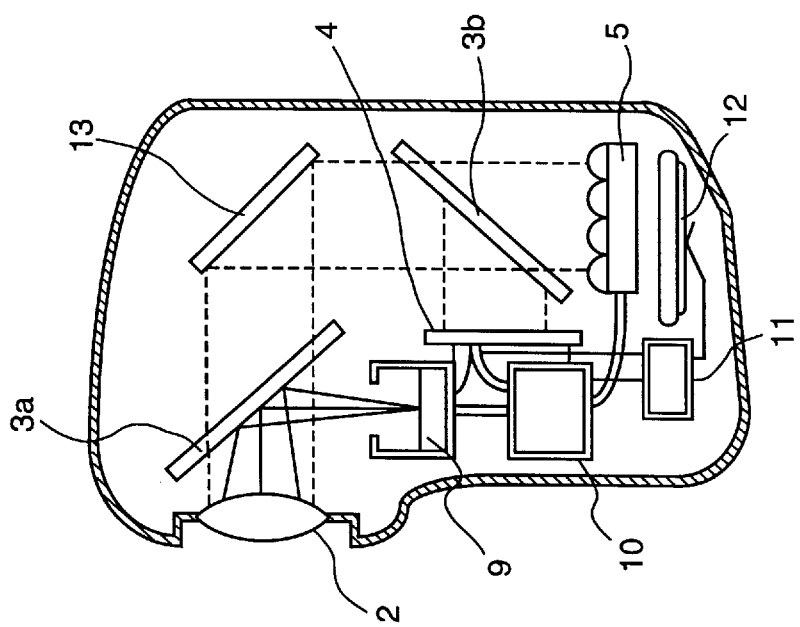
FIG. 7 is a schematic side view of a blood glucose measurement apparatus according to a second embodiment of the invention.

FIG. 7 illustrates a blood glucose measurement apparatus according to a second embodiment of the invention. Here the blood glucose measurement apparatus basically is composed of elements the same as those shown in FIG. 1. Accordingly, these elements are designated by like reference characters and need not be described again. Note also that the eye of the subject is not shown.

By using one's own eye to observe the light-emitting display panel 4 via the convex lens 2, half-mirrors 3a, 3b and mirror 13, the reference light and near-infrared measurement light, which are emitted by a light-emitting element 5 (5a, 5b) serving as irradiating means, reaches the retina 8 via the half-mirrors 3a, 3b, mirror 13, convex lens 2, cornea 6 and lens 7. The light-emitting display panel 4, light-emitting element 5 and light sensor 9, which senses the reflected-light intensity of the reference light and measurement light, are placed on the optic axis of the convex lens 2. As shown in FIG. 1, the reference light and near-infrared measurement light which has reached the retina 8 is reflectively scattered by the retina 8 so as to reach the light sensor 9 via the lens 7, cornea 6, convex lens 2 and half-mirror 3a. In the arrangement of FIG. 7, the light which reaches the light sensor 9 does not pass through the half-mirror 3a. Consequently, attenuation of the light by the half-mirror is reduced, thereby raising the detection sensitivity of the light sensor 9.

The intensity of the reflected reference light and measurement light obtained by the light sensor 9 is converted to a blood glucose value by the processing circuit 10 and the value is displayed on the light-emitting display panel 4.

These elements and circuitry are supplied with power from the battery 12 via the regulator or converter 11. The half-mirrors 3a, 3b may be beam splitters comprising dichroic mirrors or prisms to raise the efficiency with which light is utilized. Further, the blood glucose value display and data can be made transferable to a device external to the blood glucose measurement apparatus. The wavelengths and composition of the reference light and measurement light as well as the shape, size and construction of the apparatus may be modified without departing from the scope and spirit of the invention.

The blood glucose measurement apparatus according to the illustrated embodiments measures blood glucose by applying measurement to the blood vessels present on the retina of the eye. Since the walls of retinal blood vessels are comparatively transparent, blood glucose value can be measured directly using optical means. Furthermore, employing reference light makes it possible to cancel the effects of light that passes through the eyeball, thus making it possible to improve measurement accuracy. This measurement requires positional precision because the retina must be irradiated with external light via the pupil and the reflected light must be measured. Accordingly, beam splitters such as half-mirrors are placed on the optic axis of the irradiating light, the subject is allowed to observe the image of a character string or figure via the beam splitters by a light source having a wavelength different from that of the irradiating light, and the subject is capable of judging that the image is in correct focus when the image such as the character string is readable. Furthermore, by displaying the blood glucose value on the display panel 4 directly in the form of characters, the subject can read the measured value.

The present invention is not limited to the above embodiments and various changes and modifications can be made within the spirit and scope of the present invention. Therefore, to apprise the public of the scope of the present invention, the following claims are made.

What is claimed is:

1. A blood glucose measuring apparatus comprising:
   irradiating means for irradiating reference light onto blood vessels present on the retina of the eye with light from outside the cornea of the eye;
   sensing means for sensing a reflected light intensity from the blood vessels irradiated with the light from said irradiating means;
   calculating means for calculating the difference between the reference light intensity and the reflected light intensity; and
   determining means for determining a value of the amount of blood glucose by referring to a predetermined table for correlating the blood glucose amount based on the difference determined by the calculating means.

2. The apparatus according to claim 1, further comprising beam splitters disposed on the optic axis of the irradiating light from said irradiating means, wherein a person using the apparatus can observe a string of characters or figures indicative of a determined blood glucose value, via said beam splitters and wherein the string of characters or figures have a wavelength different from that of the irradiating light.

3. A blood glucose measurement apparatus comprising:
   light-emitting means for emitting light having first and second wavelengths;
   sensing means for sensing reflected-light intensity of the light of each of the first and second wavelengths emitted by said light-emitting means and reflected by the retina of the eye of a user using the apparatus; and arithmetic means for calculating a blood glucose value of the user based upon a difference between the reflected-light intensities sensed by said sensing means;

wherein an actual blood glucose value is determined from a predetermined table of differences between reflected-light intensities and actual blood glucose values.

4. The apparatus according to claim 3, wherein said light-emitting means emits light having the first and second wavelengths in a time-shared fashion, and said sensing means senses the reflected-light intensity of the light of each of the first and second wavelengths in correspondence to the light-emitting timings of the light of the first and second wavelengths.

5. The apparatus according to claim 3, further comprising a display panel for displaying the blood glucose value determined by the arithmetic means, wherein said display is adapted to be viewed by the eye which is used to determine the blood glucose value without necessarily changing the orientation of said apparatus to said eye.

6. The apparatus according to claim 3, wherein said wherein said predetermined table contains in correlated form, the difference between reflected-light intensities and their corresponding actual blood glucose values.

7. A blood glucose measurement apparatus comprising:

designating means for designating start of measurement;

light-emitting means for emitting light of first and second wavelengths which differ from each other;

driving means for starting drive of said light-emitting means in response to a designation from said designating means;

sensing means for sensing reflected-light intensity of the light of each of the first and second wavelengths emitted by said light-emitting means, which are being driven by said drive means, and reflected by the retina of the eye of a subject using the apparatus;

difference calculating means for obtaining a difference between the reflected-light intensities of the light of the first and second wavelengths sensed by said sensing means;

arithmetic means for obtaining an actual blood glucose value, by utilizing a predetermined table of conversion values, based upon the difference between the reflected-light intensities calculated by said difference calculating means; and display means for displaying the blood glucose value determined by said arithmetic means.

* * * * *